US005670652A

United States Patent [19]
Drauz et al.

[11] Patent Number: 5,670,652
[45] Date of Patent: Sep. 23, 1997

[54] METHOD OF PRODUCING OPTICALLY ACTIVE, 4-SUBSTITUTED (S)-2-OXAZOLIDINONES

[75] Inventors: Karlheinz Drauz, Freigericht; Michael Schwarm, Alzenau, both of Germany

[73] Assignee: Degussa Aktiengesellschaft, Frankfurt am Main, Germany

[21] Appl. No.: 503,225

[22] Filed: Jul. 17, 1995

[30] Foreign Application Priority Data

Jul. 15, 1994 [DE] Germany ............................ 44 25 067.3

[51] Int. Cl.$^6$ ................................................. C07D 263/22
[52] U.S. Cl. ............................................. 548/228; 560/155
[58] Field of Search .............................. 548/228; 560/155

[56] References Cited

FOREIGN PATENT DOCUMENTS

| 2540114 | 3/1984 | France . |
| 1417030 | 10/1956 | Germany . |
| WO 95/11296 | 4/1995 | WIPO . |

OTHER PUBLICATIONS

Ku et al., J. Org. Chem., 54, 3487–91 (1989).
Lubell et al., J. Am. Chem. Soc., 110, 7447–55 (1988).
Kleschick et al., J. Org. Chem., 52, 3168–69 (1987).
Sauerberg et al., J. Med. Chem., 32, 1322–26 (1989).
Fujita et al., J. Org. Chem., 53, 5415–21 (1988).
Kano et al., Tet. Lett. 28[50], 6331–34 (1987).
Bouchaudon et al., J. Chem. Soc. Perkin Trans. 1,4, 695–701 (1989).
Evans et al., J. Am. Chem. Soc., 110(4), 1238–56 (1988).
Meyers, Tetrahedron, 48(13), 2589–2612 (1992).
Lowenthal et al., Tetrahedron Lett., 31(42), 6005–8 (1990).
Zuan, et al., "Optically Active Amino . . . Acid", Chinese chemical Letters vol. 3, No. 4, pp. 237–238, 1992.
Zhang, et al., "Optically Active . . . Esters", Chinese Chemical Letters vol. 5, No. 5, pp. 373–374, 1994.
Lowenthal, et al., "Asymmetric Catalytic . . . Complexes", Tetrahedron Letters, vol. 31, No. 42, pp. 6005–6008, 1990.
Evans et al., "Pi–Solvation . . . Ubergangzustand", Ang. Chemie, Bd. 99, Nr. 11, 1987, Sieten 1197–1199.
Evans et al., "Asymmetric Diels . . . Acyloxazolidinones", J. Am. chem. Soc. 1988, 110, pp. 1238–1256.
Meyers, "Recent Progress Using Chiral . . . Syntheses", Tetrahedron vol. 48, No. 13, pp. 2589–2612, 1992.
McKennon, et al., "A Convenient Reduction of Maino Acids and Their Derivatives", J. Org. Chem. 1993, 58, pp. 3568–3571.
Evans et al. J. Am. Chem. Soc., vol. 103, No. 8, 1981, pp. 2127–2129.
Pridgen et al. J. Org. Chem., vol. 54, No. 13, 1989, pp. 3231–3233.

*Primary Examiner*—Johann Richter
*Assistant Examiner*—Laura R. Cross
*Attorney, Agent, or Firm*—Cushman Darby & Cushman IP Group of Pillsbury Madison & Sutro LLP

[57] ABSTRACT

The invention relates to a method of producing optically active, 4-substituted (S)-2-Oxazolidinones, novel (S)-2-oxazolidinones, novel, optically active (S)-amino alcohols and the use of these compounds.

6 Claims, No Drawings

METHOD OF PRODUCING OPTICALLY ACTIVE, 4-SUBSTITUTED (S)-2-OXAZOLIDINONES

The invention is relative to a method of producing optically active, 4-substituted (S)-2-oxazolidinones of general formula IV

in which R stands for a space-filling, branched alkyl group with 5–10 C atoms which contains at least one tertiary C atom, as well as novel, optically active (S)-2-oxazolidinones of general formula IV, novel, optically active (S)-amino alcohols of general formula III

in which R stands for a space-filling, branched alkyl group with 5–10 C atoms which contains at least one tertiary C atom, which compounds of formula III are interesting as intermediates for the production of the compounds of formula IV. The invention also describes the use of the novel compounds. Optically active (S)-2-oxazolidinones and the corresponding, optically active amino alcohols which appear in their synthesis as intermediate (product) are extremely important substance classes in organic chemistry. They find broad application in asymmetric synthesis, in the production of pharmaceutical active substances such as e.g. peptides, in the synthesis of insecticides, the splitting of racemic mixtures and in other areas (see for further literature on these topics, among others, J. Org. Chem. 1993, 58, 3568).

The use of optically active amino alcohols of the general formula III in asymmetric synthesis is very frequently based on the fact that amino alcohols with sterically demanding side groups are inserted into suitable derivatives with which an asymmetric catalysis or asymmetric induction is possible in the synthesis of daughter products. Examples for such amino alcohols are, among others, phenylglycinol (R=Ph), phenylalaninol (R=CH$_2$Ph), valinol (R=CHMe$_2$) and tert.-leucinol (R=CMe$_3$). These substances can be derivatized e.g. to optically active oxazolines and similar compounds which for their part can be used as ligands for highly active (potent) catalysts, e.g. in the asymmetric cyclopropanation and reduction of olefines, the hydrosilylation and reduction of ketones, in Diels-Alder reactions and nucleophilic substitutions (further literature e.g. in: Angew. Chem. 1991, 103, 556). 4-substituted 2-oxazolidinones (Org. Synth. 1989, 68, 77 and lit. cited there), bicyclic lactams (Tetrahedron 1991, 47, 9503 and lit. cited there) and formamidines (Tetrahedron 1992, 48, 2589 and lit. cited there) are named as examples for daughter products of optically active amino alcohols which can be used in many ways in asymmetric synthesis.

In the instances cited and in many others the side groups of the inserted, optically active amino alcohols of general formula III exert a directing influence for steric or stereoelectronic reasons on the reactions taking place on and with these molecules, from which the partially (at times) extremely high enantio- or diastereoselectivities of such subsequent reactions result. This directing influence is in many instances all the greater, the more space-filling the cited R side groups are (Angew. Chem. 1991, 103, 556). Thus, the e.e. or d.e. obtained is frequently greater if the side group is a tert.-butyl group (R=CMe$_3$) instead of an isopropyl group (R=CHMe$_2$) (for examples, see among others: Tetrahedron Lett. 1990, 31, 6005; Tetrahedron 1992, 48, 2589; Angew. Chem. 1987, 99, 1197; J. Am. Chem. Soc. 1988, 110, 1238).

In view of these facts, the present invention has the problem of indicating a method of producing oxazolidinones which makes accessible in particular those derivatives with space-filling side chains which exceed, if possible, the steric demand of a tert.-butyl group in order to exert an even greater directing influence in asymmetric syntheses in this manner and therewith improve the enantio- and diastereoselectivity in these reactions even more. The invention also has the problem of indicating the preparation of novel oxazolidinone compounds as well as of novel, optically active (S)-amino alcohols and their use.

These and other problems not explained in detail are solved by a method with the features of the characterizing part of claim 1. Advantageous method modifications are placed under protection in the method claims dependent on claim 1. Novel compounds constitute subject matter of claims 17 and 18.

The fact that an optically active (S)-amino alcohol of general formula III

in which R stands for a space-filling, branched alkyl group with 5–10 C atoms which contains at least one tertiary C atom, is converted in accordance with the invention into the corresponding, optically active 4-substituted (S)-2-oxazolidinone of general formula IV

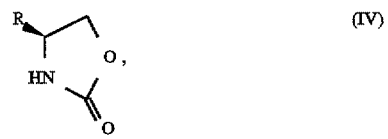

in which R has the significance indicated at III, in that the amino alcohol is acylated by reaction (conversion) with a chloroformic acid ester under pH control on the nitrogen and the intermediately formed, N-protected amino alcohol is then cyclized base-catalyzed to the (S)-2-oxazolidinones of general formula IV makes it possible under mild reaction conditions to prepare the sterically especially demanding compounds of formula IV striven for in a good yield.

The acylation is carried out in the neutral to slightly basic range in a 2-phase system of water and an organic solvent, preferably in a range of pH 6–10, especially preferably pH 7–8.5. Chloroformic acid methyl- and ethyl ester are especially preferred as chloroformic acid ester. The organic solvent must dissolve the reaction partners sufficiently well and be inert under the reaction conditions but can in principle be selected almost freely. Solvents with ether structure or hydrocarbons are preferred. It is especially preferable to use solvents which can be simultaneously used for the extraction of the amino alcohol of general formula III from aqueous phase, (for) the acylation with chloroformic acid ester, the following basic cyclization to the oxazolidinone of general formula IV and its crystallization since complicated and expensive solvent changes are then eliminated. According to the invention toluene and xylenes are quite particularly preferred for this purpose.

The cyclization can be carried out with a plurality of bases; however, according to the present invention the simplest and most economical bases, namely alkali metal hydroxides, proved to be the most suited. Sodium hydroxide is quite particularly preferred, which is again preferably used in a finely granulated or powdered form. In addition, an elevated temperature of advantageously at least 50° C. to the boiling point of the solvent used is favorable for achieving a complete cyclization. The alcohol released during the cyclization is distilled out of the reaction mixture if the reaction temperature is selected to be sufficiently high.

When the reaction is over the base is advantageously neutralized by the addition of an equivalent amount of acid, the salt washed out with water and the oxazolidinone of general formula IV isolated and purified by cooling off, evaporation to low bulk and optional recrystallization.

The optically active (S)-amino alcohols of formula III can basically be obtained from optically active L-amino acids of general formula II Compounds of formula II are preferably reduced

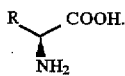   (II)

with hydridic reagents to the (S)-amino alcohols of general formula III. Reagents such as lithium aluminum hydride or especially alkali boron hydrides activated with an activator can be considered as reducing agents thereby. In the case of the alkali boron hydrides, lithium- and sodium boron hydride are preferred, of which the latter is especially preferred on account of its favorable price. 1.5–4, preferably 2–2.5 moles of the hydridic reducing agent, relative to 1 moles amino acid, are used for the reduction.

Various reagents can be considered as activators, e.g. boron trifluoride etherate, trimethylchlorosilane, iodine, chlorine, hydrogen chloride or sulfuric acid (for further literature on such reduction systems for amino acids in general: J. Org. Chem. 1993, 58, 3568), of which iodine and sulfuric acid are especially preferable. Preferably, ½ mole odine or sulfuric acid relative to 1 mole alkali boron hydride is used thereby for the activation.

Solvents with ether structure, especially 1,2-dimethoxyethane (DME) and tetrahydrofurane (THF), are particularly advantageous; however, in principle even other solvents such as alcohols or acetals can be considered for the reduction. The reduction can be carried out within a broad temperature range (approximately −20° C.—boiling temperature of the solvent used); however, it is advantageous to proceed in such a manner that a solution of the activator is added dropwise to a suspension of sodium boron hydride and the amino acid of general formula II in a suitable solvent at 0°–30° C., which activator solution is in this solvent or another suitable solvent, and thereafter the mixture is heated several hours for completion of the reaction up to a maximum of the boiling temperature of the solvent used. After the mixture has cooled off, it is made acidic by adding alcohol, then water, then acid, preferably hydrochloric acid, then alkalized, preferably with sodium hydroxide solution, and the optically active amino alcohol of general formula III extracted with a suitable organic solvent under heating, if required. It can then, if desired, be distilled for further purification, crystallized, chromatographed or converted into a crystalline salt, e.g. a hydrochloride.

On the other hand, the optically active L-amino acids of general formula II can be obtained in accordance with the invention from α-keto carboxylic acids of general formula I

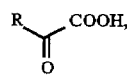   (I)

in which R stands for a space-filling, branched alkyl group with 5–10 C atoms which contains at least one tertiary C atom. This preferably takes place by means of co-factor-dependent, enzymatic, reductive amination using dehydrogenases.

It was especially surprising thereby, in no way foreseeable and especially advantageous in accordance with the invention that the enzymes used also accept α-keto acids of general formula I with their particularly space-filling R groups as substrates for the conversion into the L-amino acids of general formula II and that the products are also obtained with a high chemical and enantiomeric purity in good to very good yield.

The compounds of general formulas III and IV are novel. Compounds of general formula II are novel if R is not neopentyl (R=CH$_2$CMe$_3$).

The production of the compounds described in this invention is recapitulated in the following formula scheme:

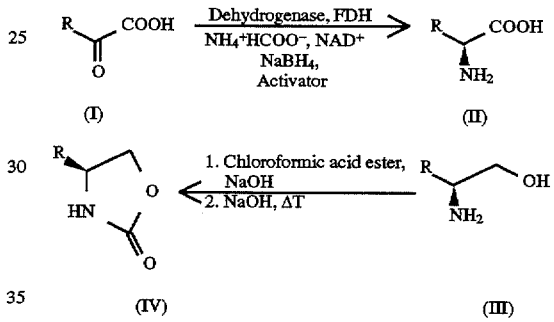

In all, novel, optically active L-amino acids of general formula II, (S)-amino alcohols of general formula III and 4-substituted (S)-2-oxazolidinones of general formula IV as well as methods are made available by the present invention, according to which these compounds can be produced in a ready and reliable manner in good to very good yield and in very high chemical and especially enantiomeric purity. The compounds produced in this manner are used, among other areas, in the synthesis of pharmaceutical active substances and in asymmetric synthesis.

The compounds of the invention and the method of their production are explained in detail by the following examples:

EXAMPLE 1

(S)-neopentylglycinol 50.8 g (0.35 mole) L-neopentylglycine were added to a suspension of 30.4 g (0.805 mole) sodium boron hydride in 250 ml DME. Then a solution of 21.5 ml (0.4025 mole) sulfuric acid in 75 ml DME was added dropwise at a maximum of 10° C. within 2.5 h and the mixture then heated 3 h to 70° C. After the mixture cooled off, 60 ml MeOH were added. The mixture was then rotated in, the residue taken up in 250 ml water and 45 ml conc. hydrochloric acid and agitated for a while. After the addition of 300 ml toluene the mixture was made basic with 65 ml 50% sodium hydroxide solution, heated to 70° C., the organic phase separated off, filtered, evaporated to low bulk (90 g) and cooled to approximately 5° C. After filtration, washing with toluene and drying in a vacuum drying oven 40.0 g (87.1%) (S)-neopentylglycinol were obtained in the form of colorless crystals.

The structure was corroborated by an NMR spectrum.

| [α]D20: +5.9° (c = 1, EtOH) Content (titration): >99% | | | | | |
|---|---|---|---|---|---|
| C7H17NO | Calc. | C 64.07 | H 13.06 | N 10.67 |
| 131.22 | Obs. | C 64.01 | H 13.13 | N 10.90 |

EXAMPLE 2

(S)-4-neopentyl-2-oxazolidinone 130 g (0.99 mole) (S)-neopentylglycinol were suspended in 700 ml toluene and 100 ml water. 99 ml (1.03 mole) chloroformic acid ethyl ester were added dropwise at 20°–25° C. within 1 h, during which the pH was maintained with 30% sodium hydroxide solution at approximately 8. After 30 min subsequent agitation the mixture was heated to 70° C. and the aqueous phase separated off. The organic phase was filtered and freed of residual water by azeotropic distillation. After the addition of 2 g granulated sodium hydroxide the mixture was slowly heated. EtOH began to distill off at 95° C., which was ended at 111° C. bottom temperature. After the mixture had cooled off to 85° C. and 3 g glacial acetic acid in 40 ml water were added, it was briefly agitated, the aqueous phase separated off and the organic phase washed again with 30 ml water. After evaporation to low bulk to 300 g and cooling overnight to approximately 5° C., 102.8 g (66.1%) (S)-4-neopentyl-2-oxazolidinone in the form of colorless crystals were obtained after removal [filtration] by suction, washing and drying. The structure was corroborated by an NMR spectrum.

| [α]D20: +9.3° (c = 1, EtOH) Melt point: 94–95° C. | | | | | |
|---|---|---|---|---|---|
| C8H15NO2 | Calc. | C 61.12 | H 9.62 | N 8.91 |
| 131.22 | Obs. | C 61.25 | H 10.02 | N 8.99 |

The mother liquor was evaporated and the residue recrystallized out of 200 ml hexane, which yielded a further 28.3 g (18.2 %) product (total yield 84.3%).

EXAMPLE 3

Synthesis of (S)-neopentylglycine 31.53 g (0.5 mole) ammonium formate and 20.89 g (125 mmole) 2 keto 4,4 dimethyl-pentanoic acid sodium salt are suspended in 400 ml of water, the pH value is adjusted with ammonia to pH 8.5 so that we have a solution and the volume is adjusted to 500 ml. Subsequently, 71.7 mg (0.1 mmole) NAD+.H2O cofactor as well as 2000 U of leucine dehydrogenase (LeuDH) and 2500 U of formate dehydrogenase (FDH) are added. The temperature is set to 28° C. The reaction is gently stirred and the pH value is adjusted to 8.2 during the reactin by a pH stat unit. As demonstrated by determining degree of conversion with HPLC, the reaction is finished after 48 h. The enzymes are separated via an ultra filter of pore size 10000 kDA and a solution is adjusted with ammonium to pH 9.5. Subsequently, the solution is clarified with 2% active charcoal and the almost colourless solution is concentrated at the rotary evaporator, the amino acid is crystallized, is separated via a funnel, is washed three times with small amounts of ethanol and is dried overnight in vacuum at 50° C.

Yield: 15.4 g (84.9% of theoretical yield)

Proof of identity: NMR spectrum

Enantiomeric purity: >99.8% e.e., as measured by chiral gas chromatography on chirasil-val.

EXAMPLE 4

Synthesis of (S)-3-methyl-isoleucine ((S)-3,3-dimethyl-norvalin)

6.3 g (0.1 mole) ammonium formate and 1.67 g (10 mmoles) 2-keto-3,3-dimethyl pentanoic acid sodium salt are suspended in 80 ml of water, the pH value is adjusted with ammonia to 8.2, so that the solids dissolve and the volume is adjusted to 100 ml. Subsequently, 14.34 mg (0.02 mmole) NAD+.3H2O cofactor as well as 800 U of leucine dehydrogenase (LeuDH) and 500 U of formate dehydrogenase (FDH) are added. The temperature is set to 32° C. During the reaction the system is gently stirred and the pH value is adjusted to 8.2 via a pH stat unit. After at most 72 h it is demonstrated via determination of degree of conversion by HPLC that the reaction is finished. The reaction solution is adjusted to pH 9.5 with ammonia and subsequently clarified with 2% active charcoal. The almost colourless solution is concentrated at a rotary evaporator, the amino acid is crystallized, is separated via a funnel, is washed three times with little ethanol and is dried overnight under vacuum at 50° C.

Yield: 1.17 g (80.6% of theoretical yield)

Proof of identity: NMR spectrum

Enantiomeric purity: >99.9% e.e., as measured by chiral gas chromatography on chirasil-val.

EXAMPLE 5

Synthesis of (S)-homoneopentylglycine ((S)-5,5-dimethyl norleucin)

Reaction and isolation were carried out analogously to example 4 with the exception that the reaction system was a suspension during the whole time of reaction and that the reaction was finished only after 96 h.

Substrate charged: 1.81 g (10 mmole) of 2-keto-5,5-dimethyl-hexanoic acid sodium salt Yield: 1.08 g (67.9% of theoretical yield)

Proof of identity: NMR spectrum

Enantiomeric purity: >99.9% e.e., as measured by chiral HPLC on Crownpak-CR+ column.

We claim:

1. A method of producing optically active, 4-substituted (S)-2-oxazolidinones of general formula IV

in which R stands for a space-filling branched alkyl group with 5–10 C atoms which contains at least one tertiary C atom, characterized in that an optically active (S)-amino alcohol of general formula III

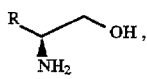 (III)

in which R stands for a space-filling, branched alkyl group with 5–10 C atoms which contains at least one tertiary C atom, is acylated with a chloroformic acid ethyl-or-methyl ester on the nitrogen and that the intermediate is cyclized with a catalytically active amount of a base to the corresponding (S)-2-Oxazolidinone of formula IV.

2. The method according to claim 1, wherein the acylation is carried out in a 2-phase system of water and an organic solvent under pH control.

3. The method according to claim 1, wherein sodium hydroxide is used as base.

4. The method according to claim 1, wherein the cyclization is carried out at a temperature between 50° C. and the boiling temperature of the organic solvent used.

5. The method according to claim 1, wherein after the end of the cyclization the base is neutralized by the addition of an equivalent amount of acid, the salt washed out of the organic solvent with water and the (S)-2-oxazolidinone of formula IV isolated by cooling off and evaporation to low bulk and, if necessary, further purified by recrystallization or chromatography.

6. The method according to claim 2, wherein the organic solvent is toluene.

\* \* \* \* \*